United States Patent [19]
Archibald et al.

[11] Patent Number: 5,854,405
[45] Date of Patent: Dec. 29, 1998

[54] CONTINUOUS PROCESS FOR DIAZOMETHANE FROM AN N-METHYL-N-NITROSOAMINE AND FROM METHYLUREA THROUGH N-METHYL-N-NITROSOUREA

[75] Inventors: Thomas G. Archibald, Fair Oaks; James C. Barnard, Shingle Springs; Harlan F. Reese, Placerville, all of Calif.

[73] Assignee: Aerojet-General Corporation, Rancho Cordova, Calif.

[21] Appl. No.: 969,993

[22] Filed: Nov. 13, 1997

[51] Int. Cl.$^6$ .................. C07C 245/12; C07C 245/16
[52] U.S. Cl. ............................. 534/565; 534/558
[58] Field of Search ....................... 534/558, 565

[56] References Cited

U.S. PATENT DOCUMENTS

| | | | |
|---|---|---|---|
| 4,197,410 | 4/1980 | Sekiya et al. | 560/159 |
| 5,459,243 | 10/1995 | Acevedo et al. | 534/565 |

FOREIGN PATENT DOCUMENTS

| | | | |
|---|---|---|---|
| 0177248 | 4/1986 | European Pat. Off. | 534/565 |
| 1033671 | 7/1958 | Germany | 534/565 |
| 63-51366 | 3/1988 | Japan | 534/565 |

OTHER PUBLICATIONS

T.H. Black *Aldrichimica Acta*, (1983) 16(1): 3–10.

*Primary Examiner*—Floyd D. Higel
*Attorney, Agent, or Firm*—Townsend and Townsend and Crew LLP

[57] ABSTRACT

Diazomethane is produced in a continuous process with little or no explosion hazard, by dissolving an N-methyl-N-nitroso amine in a mixture of a water-miscible organic solvent that dissolves the N-methyl-N-nitroso amine and a water-immiscible organic solvent that dissolves diazomethane, and combining a stream of this solution with a stream of an aqueous inorganic base, allowing the aqueous and organic phases to settle after a suitable residence time, and phase separating the phases, all on a continuous basis. When using N-methyl-N-nitrosourea as the amine, the diazomethane process is preceded by a continuous nitrosation process involving combining aqueous solutions of methyl urea and a nitrite salt with an organic solution of a mineral or organic acid, the solvent in the organic solution being a mixture of the two organic solvents referred to above, allowing the aqueous and organic phases to settle after a suitable residence time, and phase separating the phases, all on a continuous basis. The resulting organic phase is continuously fed to the diazomethane stages described above.

36 Claims, 1 Drawing Sheet

CONTINUOUS PROCESS FOR DIAZOMETHANE FROM AN N-METHYL-N-NITROSOAMINE AND FROM METHYLUREA THROUGH N-METHYL-N-NITROSOUREA

BACKGROUND OF THE INVENTION

1. Field of the Invention

This invention resides in the technology of diazomethane synthesis.

2. Description of the Prior Art

Diazomethane ($CH_2=N=N$, also known as azimethylene or diazirine) has a wide range of utility in chemical syntheses. One example of its use is as a methylating agent for carboxylic acids, phenols, alcohols, enols, and heteroatoms such as nitrogen and sulfur. Another is for the ring expansion or chain extension of ketones, and for the conversion of ketones to epoxides. A further example is its use in the conversion of acid chlorides to α-diazoketones which are themselves useful intermediates. Still further examples are its use in cycloaddition reactions with olefins to produce cyclopropyl or nitrogen-containing heterocyclic rings. Still further examples involve the formation of viral protease inhibitors including those used to combat HIV. A particularly important class of viral protease inhibitors are those that include structures known as amino acid isosteres formed by the addition of a functionalized carbon to a two-carbon amino acid. The inhibitor SAQUINAVIR® (Roche Laboratories), for example, is formed in this manner. To achieve a successful transformation, the addition of the carbon must be achieved without compromising the chirality of the amino acid or affecting any portion of the remainder of the molecule. Diazomethane meets these requirements in a modified Arndt-Eistert reaction.

A factor that limits the use of diazomethane is its hazardous nature. Diazomethane is a carcinogen, a powerful allergen, and poisonous. In addition, diazomethane is explosive. For this reason, the technical literature on the synthesis of diazomethane cautions against the use of ground-glass joints and any glassware that has not been firepolished, and no syntheses other than laboratory bench-scale syntheses have been reported. Equipment specifically designed for diazomethane preparation, such as the DIAZALD® apparatus of Aldrich Chemical Company, Inc., Milwaukee, Wis., USA, is designed for a maximum of 300 millimoles of diazomethane by single batch reaction. See Black, T. H., "The Preparation and Reactions of Diazomethane," *Aldtichimica Acta* 16(1): 3–10 (1983). A preparation referred to as "large scale" is disclosed by Acevedo et al. in U.S. Pat. No. 5,459,243, "Apparatus and Processes for the Large Scale Generation and Transfer of Diazomethane," issued Oct. 17, 1995. The reactions disclosed in the patent however are performed in laboratory Erlenmeyer glassware on a 100-millimole (4.2 g) scale.

These restrictions limit the cost effectiveness of processes for diazomethane and its use. To take full advantage of the versatility of this compound, new processes are needed that provide improvements in both yield and production rate without increasing the danger of injury to plant engineers.

SUMMARY OF THE INVENTION

It has now been discovered that diazomethane can be produced in a continuous process with little or no danger of explosion. An N-methyl-N-nitroso amine is first dissolved in a mixture of two organic solvents—one of which is at least partially water-miscible and dissolves the N-methyl-N-nitroso amine, and the other is one that is substantially less water-miscible than the first, forms a separate phase with water, and dissolves diazomethane. A stream of this solution is combined with a stream of an aqueous inorganic base, the aqueous and organic phases are permitted to settle after a suitable residence time, and the phases are separated, all on a continuous basis, the diazomethane being recovered as an organic solution. All of these stages of the process can be conducted in the liquid phase by limiting them to a temperature of less than 15° C. This avoids the formation of diazomethane vapor and allows the use of minimal head space, thereby reducing or eliminating the risk of detonation, while still producing diazomethane in high yield.

In a second aspect of this invention, N-methyl-N-nitrosourea is used as the N-methyl-N-nitroso amine and is prepared on site as part of the continuous process. Aqueous solutions of methyl urea and nitrite ion are combined with an organic solution of a mineral or organic acid, the solvent in the organic solution being the mixture of organic solvents described in the preceding paragraph, allowing the aqueous and organic phases to settle after a suitable residence time, and phase separating the phases, all on a continuous basis. The organic phase, which is a solution of N-methyl-N-nitrosourea in the organic solvents, is then combined with an aqueous organic base, the new organic and aqueous phases allowed to settle after a suitable residence time, and phase separated, all on a continuous basis and at a low temperature as described in the preceding paragraph, and diazomethane is recovered as an essentially dry organic solution.

An advantage of these continuous processes is the avoidance of the need to co-distill large amounts of organic solvent, such as ether, and diazomethane. Conducting the various stages of the process entirely in the liquid phase sharply reduces or eliminates the explosion hazard. The process further offers the advantages of continuous processes in general, including the reduction of waste by the use of recycle streams, and greater control over temperatures, concentrations, reaction times, and other process parameters. Still further features, embodiments and advantages of the invention will become apparent from the description that follows.

BRIEF DESCRIPTION OF THE DRAWING

The single drawing appended hereto is a process flow diagram illustrating one embodiment of the invention.

DETAILED DESCRIPTION OF THE INVENTION AND PREFERRED EMBODIMENTS

Figure 1:
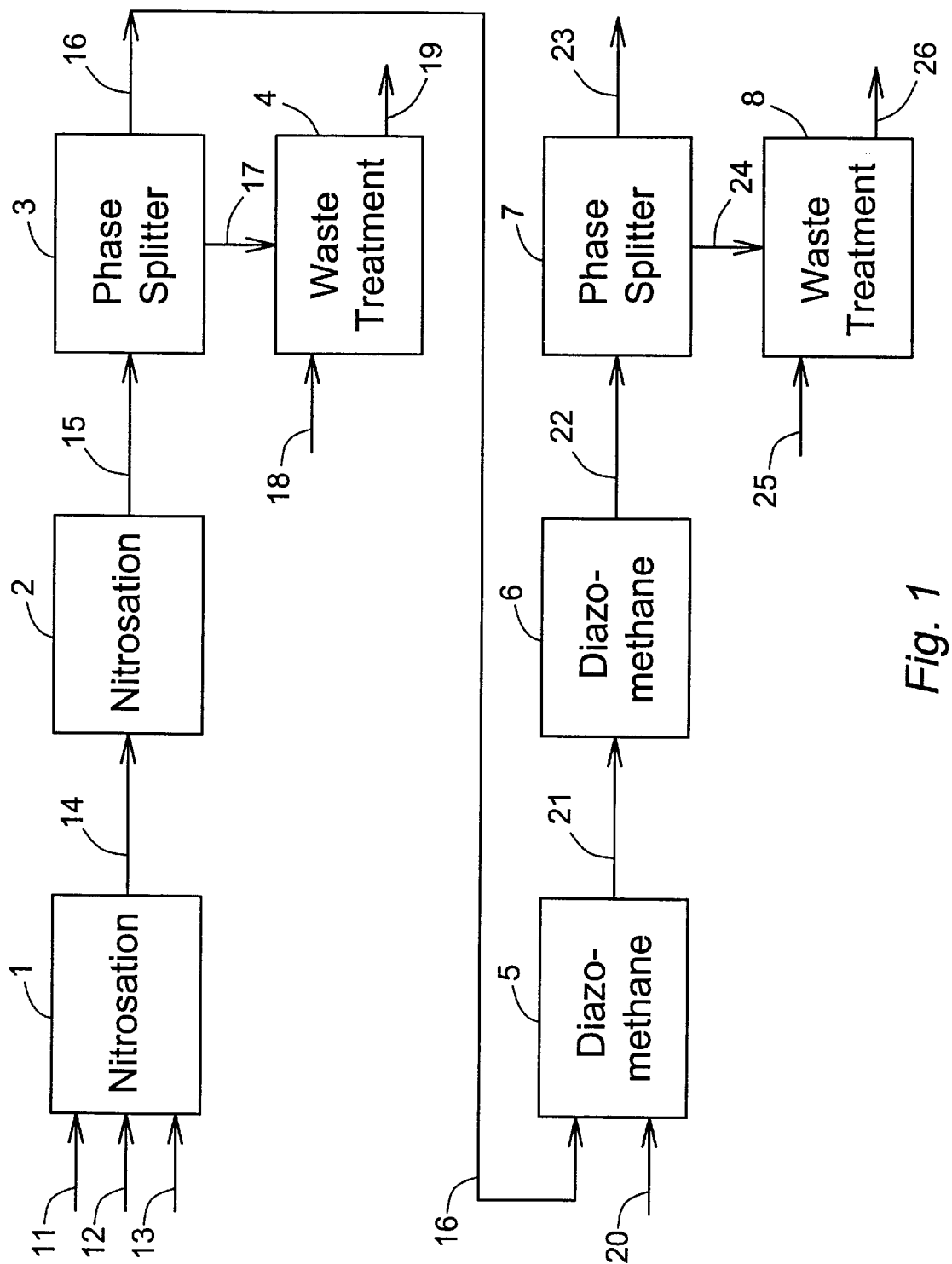

The N-methyl-N-nitroso amine used in the process of this invention is one that will react with an inorganic base at the low temperatures at which the process is conducted. Exemplary N-methyl-N-nitroso amines are those of the formula

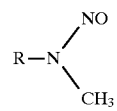

in which R is either

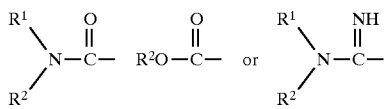

the symbol $R^1$ representing H, lower alkyl or nitro ($-NO_2-$), and $R^2$ representing H or lower alkyl. The term "lower alkyl" in this specification in its conventional sense, including both branched and unbranched alkyl groups, generally of four carbon atoms or less and preferably saturated. Preferred alkyl groups when present are unbranched, more preferably methyl or ethyl, and most preferably methyl. Examples of N-methyl-N-nitroso amines useful in this invention are N-methyl-N-nitrosourea, N,N'-dimethyl-N-nitrosourea, N-methyl-N'-nitro-N-nitrosourea, N-methyl-N-nitrosoguanidine, N,N'-dimethyl-N-nitrosoguanidine, N-methyl-N'-nitro-N-nitrosoguanidine, N-methyl-N-nitrosocarbamic acid, methyl N-methyl-N-nitrosocarbamate, and ethyl N-methyl-N-nitrosocarbamate.

The first organic solvent is one that is at least partially miscible with water, preferably with a solubility of at least about 50 parts by weight per 100 parts by weight of water, and more preferably at least about 100 parts by weight per 100 parts by weight of water, and most preferably one that is miscible in all proportions. Examples are tetrahydrofuran and methyl t-butyl ether. Tetrahydrofuran is preferred.

The second organic solvent is one that will dissolve the diazomethane when formed and extract it from the aqueous phase into a separate organic phase and whose boiling point is above the process temperatures. The solvent need not be totally immiscible with water; any solvent that will form a separate phase and extract most if not all of the diazomethane can be used. This is intended to be encompassed with the term "water-immiscible," which is used herein for convenience. The solubility of the second organic solvent in water is substantially less than that of the first solvent. The term "substantially less" in this context means that in the relative amounts used, the first organic solvent will not form a separate phase with water while the second solvent will. The difference in water miscibility is generally at least about 30 parts per 100 parts of water, by weight, preferably about 50 parts per 100 parts of water, and most preferably about 100 parts per 100 parts of water. Preferred organic solvents are those that also have vapor pressures sufficiently high that any vapor spaces in the reaction system that contain vaporized diazomethane will also contain a sufficient proportion of the solvent vapor to reduce the explosion hazard. Accordingly, preferred solvents are those whose boiling points are within the range of about 15° C. to about 40° C. Examples of suitable solvents are diethyl ether, methyl ethyl ether, and methyl propyl ether. The most preferred is diethyl ether.

The relative amounts of tetrahydrofuran and the water-immiscible organic solvent in the flowing stream(s) are not critical to the invention and can vary. The amount of tetrahydrofuran to be used is any amount that will dissolve the reactants sufficiently to result in a reaction rate fast enough to complete the reaction in an economically reasonable residence time. A contributing factor is the mixing efficiency of the reaction equipment—with the use of high-efficiency mixers, such as high-pressure static mixers or high-shear mixers, a lesser amount of tetrahydrofuran can be used. Likewise, the amount of water-immiscible organic solvent to be used is any amount that will extract all of the diazomethane produced by the reaction. A contributing factor in this regard is the flow rate of the reaction materials through the continuous-flow system—the less time allowed for phase separation, the more water-immiscible organic solvent will be needed. As indicated above, it is further preferred that sufficient organic solvent be used that the vapor phase above the liquid reaction medium is sufficiently diluted by vaporized solvent that the explosion hazard is eliminated. In most cases, best results from both functional and economic perspectives will be achieved with the two solvents in a mole ratio ranging from about 0.3:1 to about 3:1, preferably from about 0.5:1 to about 2:1, and most preferably from about 0.75:1 to about 1.33:1.

The concentration of the N-methyl-N-nitroso amine can vary, and the primary consideration is maintaining a concentration that is low enough relative to the water-immiscible organic solvent that the vapor phase concentration is below the explosive range. In preferred embodiments of the process, the N-methyl-N-nitroso amine and the water-immiscible organic solvent are used in a mole ratio of from about 0.02:1 to about 0.25:1 (amine:solvent), most preferably from about 0.10:1 to about 0.15:1.

The choice of inorganic base is not critical to the invention, although the preferred inorganic base is potassium hydroxide. The base is fed at a stoichiometric excess relative to the N-methyl-N-nitroso amine to achieve full conversion of the N-methyl-N-nitroso amine. Preferred mole ratios of the base to the amine, particularly with potassium hydroxide as the base and N-methyl-N-nitrosourea as the amine, are at least about 1.5:1, more preferably from about 1.5:1 to about 50:1, and most preferably from about 1.8:1 to about 20:1.

The temperature in the reaction stage of the process is held at about 15° C. or below, and preferably maintained within the range of about −10° C. to about +15° C., most preferably within the range of about −5° C. to about +5° C. The resulting aqueous and organic phases are likewise maintained within these ranges during both phase settling and separation and all transfers between the various stages. The residence time of the streams in the reaction stage that are needed to achieve a complete reaction before phase splitting can vary depending on the other parameters of the process, such as concentrations and temperature. In general, best results will be obtained with a residence time within the range of from about five minutes to about one hour, and preferably from about ten minutes to about thirty minutes. Agitation of the reaction mixture is also preferable.

Once the phases are separated, the aqueous phase is a waste stream containing none of the N-methyl-N-nitrosourea or the diazomethane, and primarily a cyanate salt of the inorganic base. The cyanate salt, i.e., potassium cyanate if the base used is potassium hydroxide, is readily converted by the addition of acid to the acid form, which readily decomposes. Thus, for example, treatment with hydrochloric acid will convert potassium cyanate in the stream to an acid that will decompose to ammonia and carbon dioxide, leaving a waste water stream that contains only potassium chloride and ammonium chloride.

The organic phase contains diazomethane dissolved in tetrahydrofuran and the water-immiscible solvent (preferably diethyl ether). This stream can be washed with water or concentrated caustic to remove any residual impurities. A caustic wash is preferred, since it removes any residual water to leave a stream of anhydrous (less than 0.1% water) diazomethane. The anhydrous diazomethane can be prepared to a concentration within the range of from about 2% to about 10% by weight in the organic solvents. A preferred aqueous caustic steam is 45–50% KOH, which can be recycled to the reaction stage for diazomethane generation. The anhydrous diazomethane stream left after the caustic wash can be fed directly to a batch reactor for use of the diazomethane in a subsequent reaction, or it can be combined with one or more other flowing streams in a continuous reaction. For batch reactions, the flowing diazomethane stream can be fed to one of two reactors in alternate manner to permit a reaction to occur in one and a product work-up in the other.

Continuous settling and phase separation can be achieved with conventional plant equipment, and the amount of time needed to achieve complete separation, i.e., the residence time allowed in the phase splitter before the organic phase is drawn off as a separate stream, will depend on the degree of agitation and the configuration of the phase splitter. In general, however, proper separation will be achieved with a splitter residence time of from about 3 seconds to about 1 minute, preferably from about 10 seconds to about 30 seconds. Separation is readily achieved without the aid of a surfactant. The separation and residence time can be monitored and controlled by ultrasonic level detection or other known means of level detection.

In the second aspect of this invention, the process stages identified and described above occur subsequent (downstream of) a series of stages in which N-methyl-N-nitrosourea is formed on a continuous basis by nitrosation of N-methylurea. The reaction stage of this nitrosation portion of the process involves the continuous contacting of aqueous methyl urea, aqueous nitrite ion, and an organic solution of an acid in the same organic solvent mixture that is used in the diazomethane production portion.

The nitrite ion ($NO_2$) is fed in the form of a nitrite salt, which is converted by the acid to nitrous acid ($HNO_2$), which is the active nitrosating species for the nitrosation of N-methylurea. Any nitrite salt that is susceptible to the acid in this manner can be used. A preferred example is sodium nitrite, although other nitrite salts can be used as well. Conversion of the salt to the acid is achievable by mineral and organic acids in general. Mineral acids are preferred, particularly hydrochloric acid and nitric acid. When using stainless steel reactors, nitric acid is preferred over hydrochloric acid. The acid is preferably used in stoichiometric excess relative to the nitrite salt, although the relative amounts are not critical. Typical feeds will contain the acid in a molar excess of from about 10% to about 50%. The nitrite ion is likewise preferably used in a molar excess relative to the N-methylurea, although this as well is not critical. Excesses of the nitrite ion to the N-methylurea for best results will typically be in the range of from about 3% to about 30%.

The concentrations of these materials in their respective aqueous and organic solvents can vary as well. The considerations in selecting appropriate concentrations will be primarily to control the concentration of the N-methyl N-nitrosourea intermediate in the organic phase in accordance with the safety considerations attendant upon the diazomethane reaction as discussed above. Selection of the appropriate concentration may also affect the control of the reaction rate and hence the temperature in the reaction stage. In general, however, the concentrations are not critical. In most cases, the most efficient use of reaction materials will be gained with concentrations of, for example, from about 1 M to about 10 M (aqueous) N-methylurea, from about 1 M to about 10 M of (aqueous) nitrite salt, and organic solvents in a volume ratio relative to the aqueous phases ranging from about 1.3 to about 10.0 (organic:aqueous), preferably from about 1.5 to about 5.0. The quantity of acid in the organic feed can be determined from the preferred ratios of the quantity of acid relative to nitrite salt discussed above.

The temperature in the reaction stage for the nitrosation reaction is not critical to the invention and can vary. In most cases, best results are achieved with a temperature within the range of from about 5° C. to about 30° C., and preferably from about 10° C. to about 20° C. The reaction residence time (i.e., the amount of time that the aqueous and organic phases are held in contact before transferred to the phase splitter) will be any time sufficient to achieve complete conversion of the N-methylurea to N-methyl-N-nitrosourea, and this can vary, depending on such process parameters as concentrations and temperature. In most cases, the residence time will be at least about 5 minutes, and using process parameters within the ranges set forth above, typical residence times are from about 5 minutes to about 60 minutes, with agitation. In all stages of the process where agitation is used, an agitation speed of from about 260 rpm to about 300 rpm will provide a suitable degree of phase contact.

In both the nitrosation reaction and the diazomethane reaction, the flow-through vessel in which each reaction is performed can be either a length of pipe or a tank with inlet and outlet ports. When a length of pipe is used, static mixers positioned inside the pipe can serve to provide agitation, while in a tank, agitation can be provided by mechanical stirrers. With tanks, a series of two or more tanks arranged in a cascading array can be used rather than a single tank, to provide better control over temperature and residence time. The appropriate selection will be apparent to the skilled plant design engineer.

As in the diazomethane portion of the process, continuous settling and phase separation following the nitrosation reaction can be achieved with conventional plant equipment, and the amount of time needed to achieve complete separation will depend on the degree of agitation and the configuration of the phase splitter. In general, however, proper separation will be achieved with a splitter residence time of from about 3 seconds to about 1 minute, preferably from about 10 seconds to about 20 seconds. Separation is readily achieved without the aid of a surfactant. The separation and residence time can be monitored and controlled by ultrasonic level detection or other known means of level detection.

The attached drawing depicts one example of a process flow diagram for a laboratory scale model implementing the process of this invention. The composition and temperature of each numbered stream in this flow diagram are listed in the table below.

| Process Stream Compositions and Temperatures | | | | | | | | | | | | |
|---|---|---|---|---|---|---|---|---|---|---|---|---|
| Stream: | 11 | | 12 | | 13 | | 14 | | 15 | | 16 | |
| | kg/h | mol/h | kg/h | mol/h | kg/h | mol/h | kg/h | mol/h | kg/h | mol/h | kg/h | mol/h |
| Methylurea | 6.4 | 87.1 | | | | | 0.8 | 10.4 | 0.03 | 0.44 | | |
| Water | 21.8 | 1208.7 | 21.8 | 1208.7 | 3.06 | 169.6 | 48.0 | 2663.6 | 48.2 | 2673.6 | 0.43 | 24.1 |
| $NaNO_2$ | | | 6.6 | 95.8 | | | 1.3 | 19.2 | 0.6 | 9.1 | | |

Process Stream Compositions and Temperatures -continued

| | | | | | | | | | | | |
|---|---|---|---|---|---|---|---|---|---|---|---|
| Diethyl ether | | | 52.5 | 707.7 | 52.5 | 707.7 | 52.5 | 707.7 | 50.9 | 686.5 | |
| Tetrahydro-furan | | | 52.5 | 707.7 | 52.5 | 727.4 | 52.5 | 727.4 | 48.8 | 676.5 | |
| HNO$_3$ | | | 7.1 | 113.2 | 2.3 | 36.6 | 1.7 | 26.6 | | | |
| N-methyl-N-nitrosourea | | | | | 7.8 | 76.6 | 8.9 | 86.6 | 8.9 | 86.6 | |
| NaNO$_3$ | | | | | 6.5 | 76.6 | 7.4 | 86.6 | | | |
| NaOH | | | | | | | | | | | |
| KOH | | | | | | | | | | | |
| CH$_2$N$_2$ | | | | | | | | | | | |
| KCNO | | | | | | | | | | | |
| N$_2$ | | | | | | | | | | | |
| CH$_3$OH | | | | | | | | | | | |
| KNO$_3$ | | | | | | | | | | | |
| CO$_2$ | | | | | | | | | | | |
| Temperature | 12 ± 5° C. | | 12 ± 5° C. | | 15 ± 5° C. | | 20 ± 10° C. | | 20 ± 10° C. | | 20 ± 10° C. |

| Stream: | 17 kg/h | mol/h | 12 kg/h | mol/h | 19 kg/h | mol/h | 20 kg/h | mol/h | 21 kg/h | mol/h | 22 kg/h | mol/h |
|---|---|---|---|---|---|---|---|---|---|---|---|---|
| Methylurea | 0.03 | 0.44 | 1.1 | 59.0 | 0.03 | 0.43 | | | | | | |
| Water | 47.7 | 2649.6 | | | 49.3 | 2735.1 | 17.1 | 2663.6 | 20.3 | 127.4 | 20.6 | 1144.7 |
| NaNO$_2$ | 0.63 | 9.1 | | | 0.63 | 9.1 | | | | | | |
| Diethyl ether | 1.6 | 21.2 | | | 1.6 | 21.2 | | | 50.9 | 686.5 | 50.9 | 686.5 |
| Tetrahydro-furan | 3.7 | 50.9 | | | 3.7 | 50.9 | | | 48.8 | 676.5 | 48.8 | 676.5 |
| HNO$_3$ | 1.7 | 26.6 | | | | | | | | | | |
| N-methyl-N-nitrosourea | | | | | | | | | 0.9 | 8.7 | | |
| NaNO$_3$ | 7.4 | 86.6 | | | 9.6 | 113.2 | | | | | | |
| NaOH | | | 1.1 | 26.6 | | | | | | | | |
| KOH | | | | | | | 8.8 | 156.7 | 4.4 | 78.8 | | |
| CH$_2$N$_2$ | | | | | | | | | 2.8 | 68.6 | 3.9 | 70.1 |
| KCNO | | | | | | | | | 6.3 | 86.6 | 2.8 | 66.5 |
| N$_2$ | | | | | | | | | | | 7.0 | 86.6 |
| CH$_3$OH | | | | | | | | | | | | |
| KNO$_3$ | | | | | | | | | | | 0.09 | 2.9 |
| CO$_2$ | | | | | | | | | | | 0.09 | 2.9 |
| Temperature | 15 ± 15° C. | | 20 ± 20° C. | | 20 ± 20° C. | | 10 ± 10° C. | | 0 ± 5° C. | | 0 ± 5° C. | |

| Stream: | 23 kg/h | mol/h | 24 kg/h | mol/h | 25 kg/h | mol/h | 26 kg/h | mol/h | 27 kg/h | mol/h | 28 kg/h | mol/h |
|---|---|---|---|---|---|---|---|---|---|---|---|---|
| Methylurea | 0.19 | 10.3 | 20.4 | 1134.4 | 1.9 | 105.0 | 23.6 | 1310 | | | | |
| Water | | | | | | | | | | | | |
| NaNO$_2$ | | | | | | | | | | | | |
| Diethylether | 50.4 | 679.6 | 0.51 | 6.9 | | | 0.61 | 6.9 | | | | |
| Tetrahydro-furan | 47.3 | 656.2 | 1.5 | 20.3 | | | 1.5 | 20.3 | | | | |
| HNO$_3$ | | | | | 4.4 | 70.1 | | | | | | |
| N-methyl-N-nitrosourea | | | | | | | | | | | | |
| NaNO$_3$ | | | | | | | | | | | | |
| NaOH | | | | | | | | | | | | |
| KOH | | | 3.9 | 70.1 | | | | | | | | |
| CH$_2$N$_2$ | 2.6 | 61.0 | | | | | | | 0.33 | 7.8 | 0.035 | 0.83 |

-continued

Process Stream Compositions and Temperatures

| | | | | | | | | | |
|---|---|---|---|---|---|---|---|---|---|
| KCNO | | 7.0 | | | 7.0 | | | | |
| | | | 86.6 | | | 86.6 | | | |
| $N_2$ | | | | | | | 0.044 | | 0.037 |
| | | | | | | | | 1.6 | | 1.3 |
| $CH_3OH$ | 0.11 | | 0.02 | | 0.018 | | | | |
| | | 3.5 | | 0.55 | | | 0.55 | | |
| $KNO_3$ | | | | | | | 7.1 | | |
| | | | | | | | 70.1 | | |
| $CO_2$ | | | | | | | | | |
| Temperature | 0 ± 5° C. | | −10 ± 5° C. | | −10 ± 5° C. | | 20 ± 20° C. | | 20 ± 20° C. |

| Stream: | 29 |
|---|---|
| | kg/h |

| | mol/h | |
|---|---|---|
| Methylurea | | |
| Water | | |
| $NaNO_2$ | | |
| Diethyl ether | | |
| Tetrahydro-furan | | |
| $HNO_3$ | | |
| N-methyl-N-nitrosourea | | |
| $NaNO_3$ | | |
| NaOH | | |
| KOH | | |
| $CH_2N_2$ | 0.209 | |
| | | 5.0 |
| KCNO | | |
| $N_2$ | 0.015 | |
| | | 0.55 |
| $CH_3OH$ | | |
| $KNO_3$ | | |
| $CO_2$ | | |
| Temperature | | |

Vessels 1 and 2 of the flow diagram are flow-through reaction vessels, each equipped with a stirrer, vessel 1 representing the first of two stages of the nitrosation reaction and vessel 2 the second stage. Vessel 1 is fed by three streams—methylurea dissolved in water 11, sodium nitrite dissolved in water 12, and 70% nitric acid in water, tetrahydrofiran and diethyl ether 13. Residence time in vessel 1 is 10.0 minutes at 12° C. ±3° C. The intermediate stream 14 transfers the product from vessel 1 to vessel 2, where the residence time is an additional 10.0 minutes at the same temperature. The fully nitrosated product 15 is then transferred to a phase splitter 3 where the residence time is 5.0 to 10.0 minutes and the temperature is maintained at 20° C. ±10° C. The organic phase 16 containing the N-methyl-N-nitrosourea and the aqueous phase 17 are drawn off separately. The aqueous phase 17 is directed to a waste treatment vessel 4 to which aqueous caustic solution 18 is added to prepare a treated aqueous waste stream 19.

The organic phase 16 is directed to the first vessel 5 of two staged flow-through reaction vessels 5, 6, where the organic phase is contacted with aqueous potassium hydroxide 20. The residence time in the two vessels 5, 6 is 6.7 minutes each and the temperature in each is maintained at 0° C. ×5° C. The two-phase product stream 22 passes into a phase splitter 7 where the residence time is 4.5 minutes and the temperature is maintained at −10° C. ±5° C. The separated organic phase 23 contains the diazomethane dissolved in ether and tetrahydrofuran, and the aqueous phase 24 is directed to an aqueous waste treatment vessel 8, where nitric acid 25 is added to prepare a second treated aqueous waste steam 26.

The foregoing is offered primarily for purposes of illustration. It will be readily apparent to those skilled in the art that the operating conditions, materials, proportions and procedural steps and other parameters of the process described herein may be further modified or substituted in various ways without departing from the spirit and scope of the invention.

We claim:

1. A continuous process for production of diazomethane, comprising:

(a) continuously contacting
      (i) an organic solution comprising an N-methyl-N-nitroso amine dissolved in a mixture of a first organic solvent that is at least partially water-miscible and dissolves said N-methyl-N-nitroso amine and a second organic solvent that is substantially less water-miscible than said first organic solvent and forms a separate phase when contacted with water, said first organic solvent and said second organic solvent being in a mole ratio of from about 0.3:1 to about 3:1 and said N-methyl-N-nitroso amine having the formula

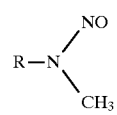

in which R is a member selected from the group consisting of

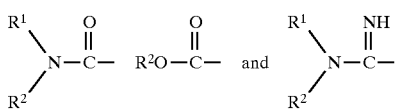

in which R¹ is a member selected from the group consisting of H, lower alkyl, and nitro, and R² is a member selected from the group consisting of H and lower alkyl, with (ii) an aqueous solution of an inorganic base, at relative flow rates such that said inorganic base is in stoichiometric excess of said N-methyl-N-nitroso amine, at a temperature of from about −10° C. to about +15° C., and for a contact time of at least about five minutes, to form a product mixture;

(b) continuously settling said product mixture into (i) an organic phase containing diazomethane produced from said N-methyl-N-nitroso amine by reaction with said inorganic base and (ii) an aqueous phase, while maintaining said phases at a temperature of from about −10° C. to about +15° C.; and (c) continuously isolating said organic phase from said aqueous phase.

2. A process in accordance with claim 1 in which said first organic solvent is tetrahydrofuran.

3. A process in accordance with claim 1 in which said second organic solvent has a boiling point of from about 15° C. to about 40° C.

4. A process in accordance with claim 1 in which said second organic solvent is a member selected from the group consisting of diethyl ether, methyl ethyl ether, and methyl propyl ether.

5. A process in accordance with claim 1 in which said second organic solvent is diethyl ether.

6. A process in accordance with claim 1 in which said first organic solvent is tetrahydrofuran and said second organic solvent is diethyl ether.

7. A process in accordance with claim 3 in which said N-methyl-N-nitroso amine and said second organic solvent are present in said organic solution at a mole ratio of from about 0.02:1 to about 0.25:1.

8. A process in accordance with claim 3 in which said N-methyl-N-nitroso amine and said second organic solvent are present in said organic solution at a mole ratio of from about 0.10:1 to about 0.15:1.

9. A process in accordance with claim 1 in which said temperature of (a) and said temperature of (b) are both from about −5° C. to about +5° C.

10. A process in accordance with claim 1 in which said contact time of (a) is from about five minutes to about one hour.

11. A process in accordance with claim 1 in which said contact time of (a) is from about ten minutes to about thirty minutes.

12. A process in accordance with claim 1 in which (a) is performed with continuous agitation.

13. A process in accordance with claim 1 in which R¹ is a member selected from the group consisting of H, methyl and nitro, and R² is a member selected from the group consisting of H and methyl.

14. A process in accordance with claim 1 in which N-methyl-N-nitroso amine is N-methyl-N-nitrosourea.

15. A process in accordance with claim 1 in which said inorganic base is potassium hydroxide.

16. A process in accordance with claim 15 in which said relative flow rates of (a) are such that said potassium hydroxide is fed at a mole ratio of at least about 1.5:1 relative to said N-methyl-N-nitroso amine.

17. A process in accordance with claim 15 in which said N-methyl-N-ntitroso amine is N-methyl-N-nitrosourea, and said relative flow rates of (a) are such that said potassium hydroxide is fed at a mole ratio of from about 1.5:1 to about 50:1 relative to said N-methyl-N-nitrosourea.

18. A process in accordance with claim 15 in which said N-methyl-N-nitroso amine is N-methyl-N-nitrosourea, and said relative flow rates of (a) are such that said potassium hydroxide is fed at a mole ratio of from about 1.8:1 to about 20:1 relative to said N-methyl-N-nitrosourea.

19. A continuous process for the production of diazomethane, comprising:

(a) continuously contacting
  (i) an aqueous solution of methyl urea,
  (ii) an aqueous solution of a nitrite ion, and
  (iii) an organic solution of an acid in a mixture of a first organic solvent that is at least partially water-miscible and dissolves N-methyl-N-nitrosourea and a second organic solvent that forms a separate phase when contacted with water, said first organic solvent and said second organic solvent being in a mole ratio of from about 0.3:1 to about 3:1, said acid being in stoichiometric excess relative to said nitrite ion, and said nitrite ion being in molar excess relative to said methyl urea,
to form a first product mixture in which a substantial portion of said methyl urea is converted to N-methyl-N-nitrosourea;

(b) continuously settling said first product mixture into (i) a first organic phase containing said N-methyl-N-nitrosourea and (ii) a first aqueous phase;

(c) continuously isolating said first organic phase from said first aqueous phase;

(d) continuously contacting said first organic phase, thus isolated, with an aqueous solution of an inorganic base, at relative flow rates such that said inorganic base is in stoichiometric excess of said N-methyl-N-nitrosourea, at a temperature of from about −10° C. to about +15° C., and for a contact time of at least about five minutes, to form a second product mixture;

(e) continuously settling said second product mixture into (i) a second organic phase containing diazomethane produced from said N-methyl-N-nitrosourea by reaction with said inorganic base and (ii) a second aqueous phase, while maintaining said second organic and aqueous phases at a temperature of from about −10° C. to about +15° C.; and (f) continuously isolating said second organic phase from said second aqueous phase.

20. A process in accordance with claim 19 in which (a) is performed at a temperature of from about 5° C. to about 30° C.

21. A process in accordance with claim 19 in which (a) is performed at a temperature of from about 10° C. to about 20° C.

22. A process in accordance with claim 19 in which (a) is performed with a contact time of at least about 5 minutes with agitation.

23. A process in accordance with claim 19 in which (a) is performed with a contact time of from about 10 minutes to about 60 minutes with agitation.

24. A process in accordance with claim 19 in which said aqueous solution of nitrite ion is an aqueous solution of sodium nitrite, and said acid is a member selected from the group consisting of hydrochloric acid and nitric acid.

25. A process in accordance with claim 19 in which said aqueous solution of nitrite ion is an aqueous solution of sodium nitrite, and said acid is nitric acid.

26. A process in accordance with claim 19 in which said nitrite ion and said acid of (a) are both used at stoichiometric excesses relative to said methyl urea.

27. A process in accordance with claim 19 in which said first organic solvent is tetrahydrofuran.

28. A process in accordance with claim 19 in which said second organic solvent has a boiling point of from about 15° C. to about 40° C.

29. A process in accordance with claim 19 in which said second organic solvent is a member selected from the group consisting of diethyl ether, methyl ethyl ether, and methyl propyl ether.

30. A process in accordance with claim 19 in which said second organic solvent is diethyl ether.

31. A process in accordance with claim 19 in which said first organic solvent is tetrahydrofuran and second organic solvent is diethyl ether.

32. A process in accordance with claim 19 in which said temperature of (d) and said temperature of (e) are both from about −5° C. to about +5° C.

33. A process in accordance with claim 19 in which said contact time of (a) is from about 5 minutes to about 60 minutes.

34. A process in accordance with claim 19 in which said contact time of (a) is from about 10 minutes to about 30 minutes with continuous agitation.

35. A process in accordance with claim 19 in which said inorganic base is potassium hydroxide.

36. A process in accordance with claim 19 in which said aqueous solution of nitrite ion is an aqueous solution of sodium nitrite, said acid is nitric acid, said second organic solvent is diethyl ether, and said inorganic base is potassium hydroxide.

* * * * *